(12) United States Patent
Luevano et al.

(10) Patent No.: US 8,585,592 B2
(45) Date of Patent: Nov. 19, 2013

(54) MEDICAL DEVICE WITH A FITTING HAVING A GAS VENTING POSITION

(75) Inventors: Charles A. Luevano, Ann Arbor, MI (US); David M. Fallen, Asheville, NC (US)

(73) Assignee: Terumo Cardiovascular Systems Corp., Ann Arbor, MI (US)

( * ) Notice: Subject to any disclaimer, the term of this patent is extended or adjusted under 35 U.S.C. 154(b) by 527 days.

(21) Appl. No.: 12/887,838

(22) Filed: Sep. 22, 2010

(65) Prior Publication Data

US 2012/0071736 A1 Mar. 22, 2012

(51) Int. Cl.
*A61B 5/00* (2006.01)
*G01N 15/06* (2006.01)
*G01N 21/00* (2006.01)

(52) U.S. Cl.
USPC ........ 600/309; 600/310; 422/68.1; 422/82.05

(58) Field of Classification Search
USPC ................. 600/310, 322, 344, 309, 473, 476; 356/39, 244, 246; 422/44, 68.1, 55, 422/102, 104, 82.05; 436/63, 66, 68, 172
See application file for complete search history.

(56) References Cited

U.S. PATENT DOCUMENTS

| 3,941,132 | A | * | 3/1976 | Lenaghan | 604/377 |
| 4,516,974 | A | * | 5/1985 | Davis | 604/333 |
| 5,469,841 | A | * | 11/1995 | Kobayashi et al. | 600/158 |
| 5,997,818 | A | | 12/1999 | Hacker et al. | |
| 7,503,905 | B2 | | 3/2009 | Jessop et al. | |
| 7,731,155 | B2 | | 6/2010 | Funamura et al. | |

* cited by examiner

*Primary Examiner* — Tse Chen
*Assistant Examiner* — Chu Chuan (JJ) Liu
(74) *Attorney, Agent, or Firm* — Gael Diane Tisack; Darryl Newell; MacMillan, Sobanski & Todd

(57) ABSTRACT

A blood parameter measurement cassette or other device is configured to control incidental liquid discharged during the device's calibration process. The cassette includes optical sensors which are chemically responsive to blood constituents and require calibration with a blood parameter monitoring device prior to use in a medical procedure. During the calibration process, an incidental amount of a liquid may be expelled from the cassette. The present invention is directed towards controlling the expelled liquid by absorbing it using an absorbent material disposed on the exterior of the cassette's main body. The absorbent material thereby prevents the liquid from causing detrimental effects to the monitoring and calibration equipment used in conjunction with the cassette. The scope includes additional embodiments wherein the inventive concept is applied to other fluid-handling medical devices that require venting of gases.

5 Claims, 3 Drawing Sheets

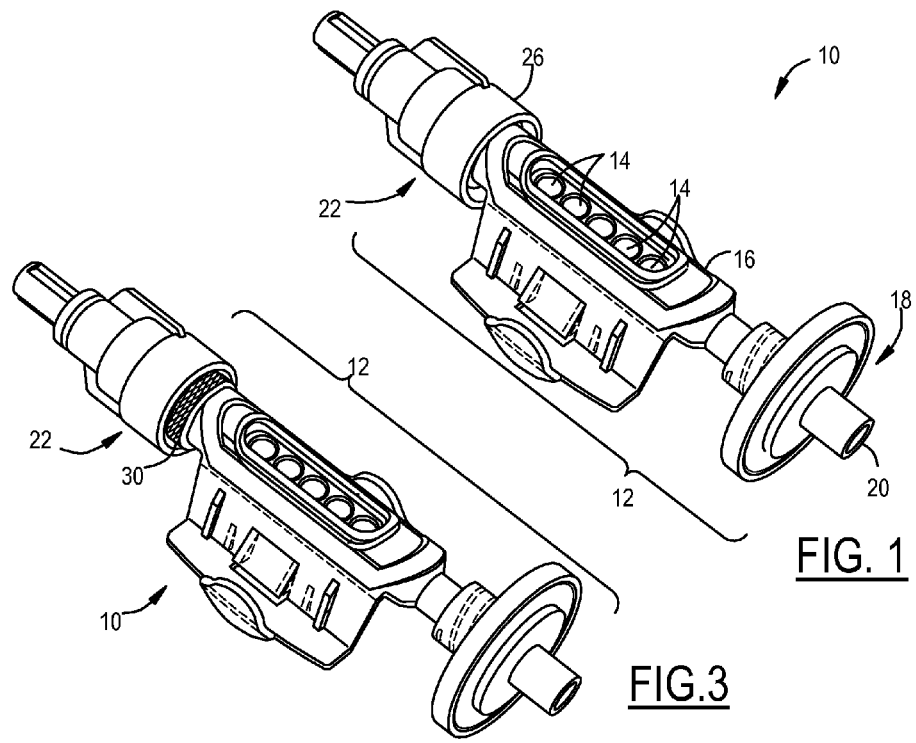
FIG. 1
FIG. 3
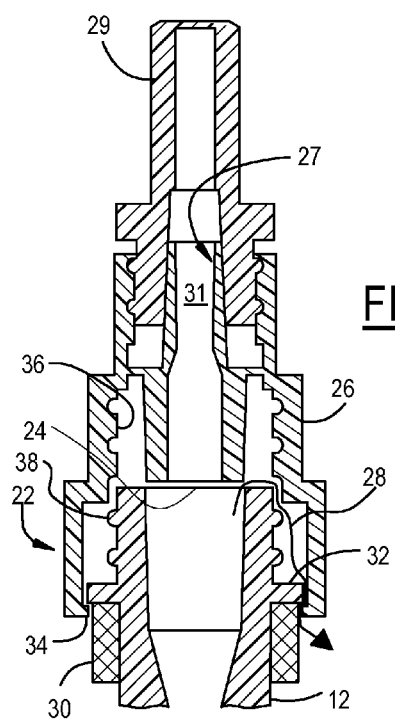
FIG. 4
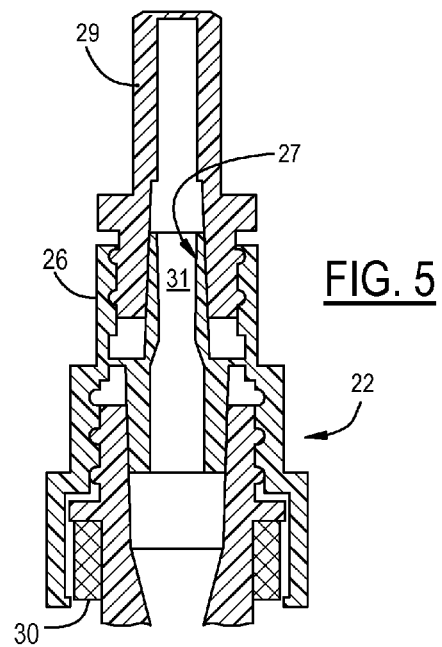
FIG. 5

MEDICAL DEVICE WITH A FITTING HAVING A GAS VENTING POSITION

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

1. Field of the Invention

The present invention relates to controlling liquid discharged from a blood parameter measurement cassette or other device during venting of the device while calibrating it by passing calibration gas through the device, and more generally to controlling incidental liquid discharged during a venting process of fluid-handling medical devices.

2. Description of the Related Art

Medical devices are often used during certain surgical procedures when various characteristics or parameters of blood are monitored in real time. For example, during open heart surgery the surgeon and other members of the surgical team often monitor the pH of the patient's blood as well as the concentration of certain blood gases such as carbon dioxide and oxygen. Measurement of blood parameters is often accomplished using optical sensors installed in a cassette connected to an extracorporeal blood circuit in fluid communication with the vascular system of the patient.

For best results, the optical sensors of blood parameter measurement systems require calibration before use. One calibration technique, described in U.S. Pat. No. 5,997,818 to Hacker which is incorporated herein by reference in its entirety, involves bubbling calibration gases through a sterile liquid in the cassette chamber to calibrate the optical sensors to a blood parameter monitoring device. The calibration gas is vented to atmosphere after bubbling through the liquid. An incidental vestige of liquid may expel from the chamber along with the calibration gas as it is vented from the chamber to the atmosphere.

Expelled liquid is undesirable since it may migrate into sensitive areas of the blood parameter monitoring device components and potentially cause negative effects to the electronic or optical equipment. However, the current state of the art allows incidental amounts of liquid to be expelled and potentially affect the monitoring and calibration equipment used in conjunction with the cassettes.

From a broader perspective, many medical devices that receive a liquid flow require a venting process before the device is used in a medical procedure to remove air or other gases that may be contained within the interior of the device. If the gas is not removed prior to use, the safety and/or efficacy of the medical procedure may be negatively affected. For example, gas bubbles inside a medical device may collect in the area of highest elevation within the device and impede the liquid flow thereby reducing the performance of the device. In addition, the gas could be inadvertently injected into a patient, resulting in known health risks.

Generally, whenever medical devices require a venting process to remove internal gases from a liquid, some potential exists for an incidental amount of the liquid to discharge from the device along with the gas. Discharged liquid related to venting can be problematic in the medical setting because of issues such as blood borne pathogens, cross-contamination of substances, slip and fall injuries, damage to sensitive equipment, and other safety concerns. A means for controlling the liquid discharged caused by a venting process would be beneficial to patients and practitioners in the medical setting.

SUMMARY OF THE INVENTION

The present invention in one aspect concerns an improved blood parameter measurement cassette. The cassette includes optical sensors which are chemically responsive to blood constituents during a medical procedure. The sensors require calibration prior to use in a procedure. During the calibration process, an incidental amount of a liquid may be expelled from the cassette, as described below. The present invention is directed towards controlling the expelled liquid to prevent it from causing detrimental effects to the monitoring and calibration equipment used in conjunction with the cassettes.

The main body of a blood parameter measurement cassette has a longitudinal axis that is oriented substantially vertically during the calibration process. In the vertical orientation, cassettes have a first port at their lower end, and a second port at their upper end. Between the upper and lower ports resides a middle chamber containing a liquid buffer solution that facilitates the calibration process. The cassette manufacturer furnishes the cassettes with the liquid pre-installed in the middle chamber.

The cassette has a fitting coupled to the second port. The fitting is movable between a first closed position and a second venting position. While in the venting position an egress path is defined by the space between the cassette's main body and the fitting. The egress path is used during the calibration process to allow calibration gas to flow or vent from inside the cassette to the atmosphere.

During the calibration process, the first port is used as a calibration gas inlet port for connection to a source of calibration gas from a calibrator device. The second port is used as a gas outlet port for venting the calibration gas to atmosphere. As the calibration gas vents from the cassette, it may induce an incidental amount of the liquid to expel from the main body through the gas outlet port.

In order to control the expelled liquid, an absorbent material member is disposed on the periphery of the main body of the cassette at least partially in the egress path. During the calibration process the absorbent material permits calibration gas to vent to atmosphere but absorbs and retains the liquid expelled from the cassette's main body in association with the venting of the calibration gas. The absorbent material thereby mitigates the detrimental effects that may be caused by the liquid if it were to come in contact with the monitoring and calibration equipment used in conjunction with the cassettes.

The present invention is also directed to other fluid-handling medical devices that have a fitting used for venting air or other gases from their interior to atmosphere. These medical devices may exhibit an adverse discharge of liquid during the venting process. An absorbent material member disposed on the exterior of the medical device at least partially in the egress path of the gas and liquid will allow gas to vent to atmosphere while absorbing liquid. The detrimental effects of the discharged liquid generated during a venting process will thereby be mitigated.

BRIEF DESCRIPTION OF THE DRAWINGS

FIG. 1 is a perspective view of a prior art blood parameter measurement cassette.

FIG. 3 is a perspective view of a cassette having an absorbent material as in the present invention.

FIG. 4 is a longitudinal cross-sectional view of the upper end of a cassette in the venting position showing details of the fitting used for venting the cassette and the placement of the absorbent material on the periphery of the main body.

FIG. 5 is a longitudinal cross-sectional view of the upper end of a cassette in the closed position showing details of the fitting used for venting the cassette and the placement of the absorbent material on the periphery of the main body.

DETAILED DESCRIPTION OF PREFERRED EMBODIMENTS

Figure 2:
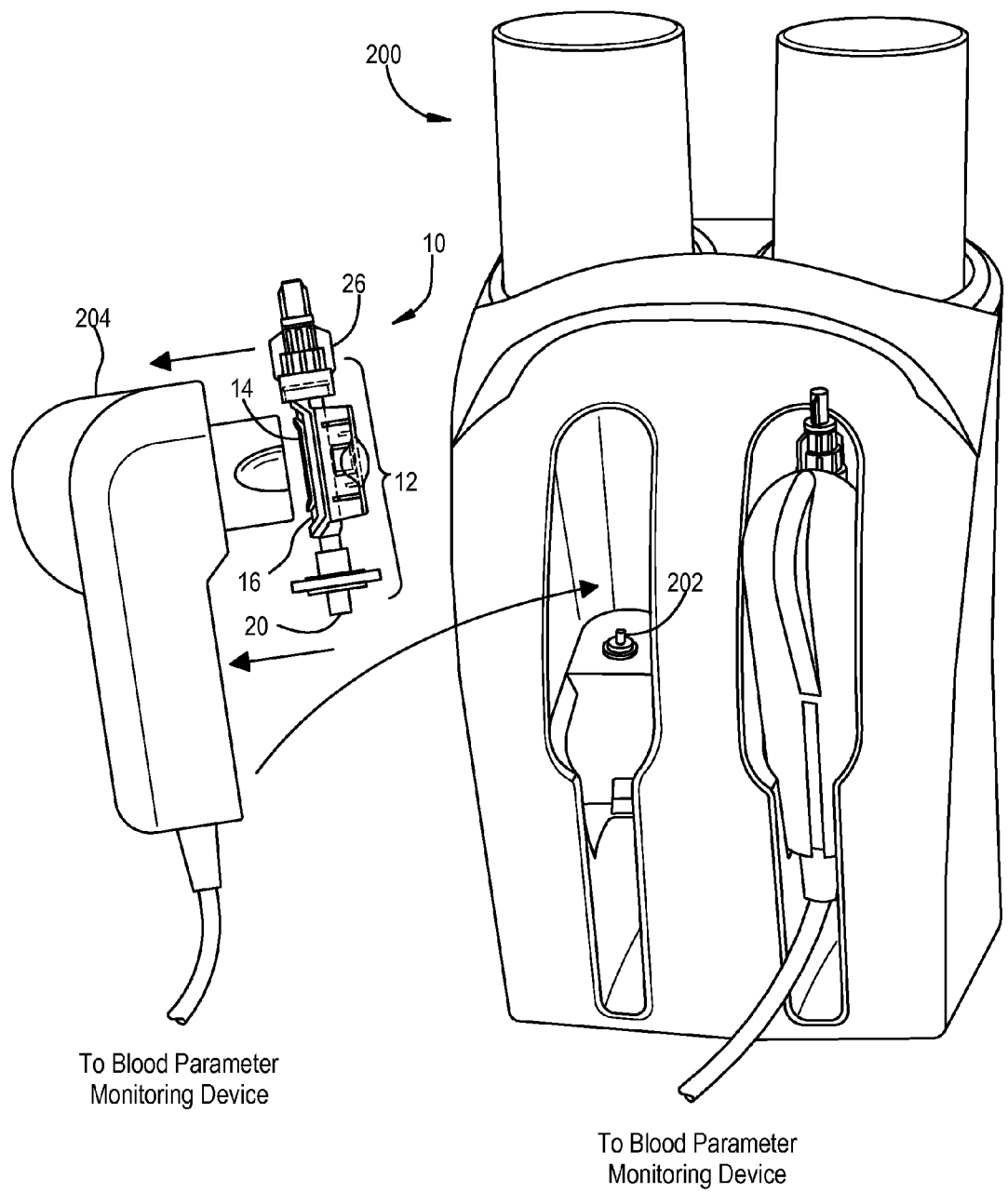
FIG. 2 is a perspective elevation view illustrating the coupling of a cassette to a probe and the insertion of the cassette/probe combination into a calibrator.

A prior art blood parameter measurement cassette 10 for measuring one or more parameters of blood is illustrated in FIG. 1. Cassette 10 broadly includes main body 12 with optical sensor(s) 14 and fitting 26.

Main body 12 includes an elongated casing having wall sections defining an elongated, internal, flow-through middle chamber 16 that extends along the longitudinal axis of main body 12. Main body 12 further includes lower end 18 having a first or inlet port 20 for admitting fluid into middle chamber 16 and upper end 22 having a second or outlet port 24 (shown in FIG. 4) for allowing fluid to exit middle chamber 16. Optical sensor(s) 14 for measuring one or more parameters of blood may include a potassium sensor, a pH sensor, a carbon dioxide sensor, and an oxygen sensor that are arranged in an aligned, spaced-apart relationship on an interior surface along the longitudinal axis of middle chamber 16 as further described in U.S. Pat. No. 5,997,818 to Hacker.

Fitting 26 has an internal threaded section that matingly receives an external threaded section disposed at upper end 22 of main body 12. The threaded engagement of fitting 26 to main body 12 enables fitting 26 to be movable with respect to main body 12 between a first closed position and a second venting position. In a preferred embodiment, fitting 26 is a luer connector type fitting.

In reference to FIG. 2, the optical sensor 14 calibration procedure will now be explained. Prior to actual use of blood parameter measurement cassette 10 for a medical procedure, optical sensor(s) 14 must be calibrated with a blood parameter monitor device (not shown). Cassette 10 comes from the cassette manufacturer with a sterile liquid buffer solution in middle chamber 16. The calibration process involves mixing and dissolving gases having known concentrations of oxygen and carbon dioxide with the liquid. Sensor(s) 14 detect the partial pressures of the oxygen and carbon dioxide in the liquid and send corresponding signals to the monitoring device via probe(s) 204. Since the concentrations of oxygen and carbon dioxide within the calibration gas are known by the monitoring device, the monitoring device can establish calibration factors to thereby reconcile any differences between the known and measured values. The calibration factors are used during the subsequent medical procedure wherein the optical sensors having been calibrated are utilized.

As FIG. 2 shows, calibration of cassettes 10 is performed by a system comprising calibrator 200 having supplies of known gases and one or two probes 204 in communication with a blood parameter monitor device (not shown). Cassettes 10 are specially designed to be mechanically coupled with probes 204 so as to ensure the cassette's optical sensor(s) 14 are properly adjacent to coordinating fiber optic bundles in probes 204 when in the coupled relationship with cassette 10. After coupling is cassettes 10 to probes 204, the combination is inserted into calibrator 200. First port 20 of cassette 10 is positioned to mate with source of calibration gas 202 in calibrator 200 as the probe/cassette combination is inserted into calibrator 200. This connection ensures source of calibration gas 202 is in fluid communication with cassette 10.

During calibration, cassettes 10 are oriented in an upright, preferably vertical position as shown in FIG. 2. Middle chamber 16 contains enough volume of sterile liquid to ensure all optical sensors 14 are in contact with liquid.

Fitting 26 is then partially unthreaded by rotating fitting 26 relative to main body 12 in an arc about the longitudinal axis of main body 12. During such motion, fitting 26 is moved from a first closed position to a second venting position for venting the gas to atmosphere. Loosening of the fitting 26 relative to main body 12 creates an egress path to enable calibration gas to flow from main body 12 to the atmosphere.

A supply of calibration gas can then begin flowing. The gas flows from source of calibration gas 202, through the cassette's first port 20, into middle chamber 16, i.e. bubbling through the liquid, through second port 24 (shown in FIG. 4), through the space between fitting 26 and upper end 22 of main body 12, and out to atmosphere. The gas supply creates gas bubbles as it flows up through the liquid in main chamber 16. The gas bubbles burst as they emerge from the upper surface of the liquid in main chamber 16. The bursting of the gas bubbles may cause a vestige of liquid to be entrained with the gas flow as it proceeds towards venting from cassette 10. In prior art devices, this vestige of liquid could make its way completely out of cassette 10 and come to rest on surfaces of probes 204 or calibrator 200. This liquid may be detrimental to the electronics or optics of probes 204 or calibrator 200. When the calibration process is complete, fitting 26 is returned to its closed position. The probe/cassette combination is then removed from calibrator 200 and is ready for actual use in a medical procedure with a blood parameter monitoring device.

FIG. 3 shows the improved blood parameter measurement cassette 10 of the present invention. Absorbent material member 30 is disposed at least partially in the is egress path of the venting gas and accompanying vestige of liquid. Absorbent material 30 will absorb liquid but allow the gas to flow away from cassette 10 to atmosphere. Absorption of the liquid by absorbent material 30 will prevent the liquid from detrimentally affecting the monitoring and calibration equipment used in conjunction with the cassettes.

In a preferred embodiment, absorbent material 30 is comprised of a strip of medical grade gauze, such as Stratex material from DelStar Technologies, Inc. of Middletown, Del. The strip of absorbent material 30 is wrapped around the outer periphery of main body 12 to substantially surround it. In this embodiment absorbent material 30 may be affixed to main body 12 by use of a medical grade adhesive. In another embodiment absorbent material 30 may be comprised of a stretchable ring of absorbent material. The stretchable ring of absorbent material 30 will have an unstretched inner diameter that is smaller than the outer diameter of main body 12 at the location where the ring is disposed. This diametrical relationship creates an interference fit and the elasticity of the ring of absorbent material will retain it in the proper location. The stretchable ring of absorbent material 30 may be installed by simply stretching it over upper end 22 of the cassette and positioning it at the proper position on the outer periphery of main body 12 as shown in FIG. 3 (e.g., prior to the installation of fitting 26 onto main body 12).

FIG. 4 is a longitudinal cross-section view of the cassette's upper end 22 and fitting 26. Fitting 26 is shown in the second venting position. In this view, the main body's second port 24 can be visualized. As shown, fitting 26 has internal threaded portion 36 that matingly receives external threaded portion 38 of upper end 22 of main body 12. Fitting 26 has a luer connector portion 27, and is adapted by threading to receive a removable cap 29 which selectably closes off a central fluid path 31 that extends through luer connector portion 27. Egress path 28 is defined by the space between the cassette's upper end 22 and fitting 26 so that gasses can be vented without opening the main central fluid path 31. When in the venting position of FIG. 4, fitting 26 has its lower end longitudinally displaced in an upward direction to expose absorbent member 30 while simultaneously opening up egress path 28. Absorbent member 30, shown in cross-section, is disposed on the outer periphery of main body 12 at least partially in egress path 28 and adjacent to annular flange 32 which is disposed on the exterior periphery of main body 12 adjacent to threaded portion 38 of upper end 22. Fitting 26 includes annular shoulder 34 disposed on the interior periphery of the fitting's lower end. The outer diameter of flange 32 is slightly larger than the inner diameter of shoulder 34. This diametrical relationship results in a physical interference between the main body's flange 32 and fitting's shoulder 34 and functions as a stop in order to prevent detachment of fitting 26 from main body 12. However, the flexible materials of fitting 26 and shoulder 34 allow fitting 26 to be removed and/or replaced from main body 12 by overcoming the interference fit with the application of a small amount of manual force.

FIG. 5 is a longitudinal cross-section view of the cassette's upper end 22 and fitting 26. Fitting 26 is shown in the closed position wherein fitting 26 has its lower end longitudinally displaced in a downward direction to cover absorbent member 30 while simultaneously closing egress path 28. This view illustrates that at least a portion of the space occupied by absorbent material 30 when fitting 26 is in the venting position (shown in FIG. 4) is preserved when fitting 26 is alternately located in the closed position. This preservation of space enables absorbent material 30 to substantially retain the liquid it absorbed during the calibration venting process when fitting 26 was in the open or venting position (i.e. it is not squeezed out). The retention of the liquid in absorbent material 30 thereby prevents the problems associated with liquid contamination of probes 204 or calibrator 200 as described above.

Figure 6:
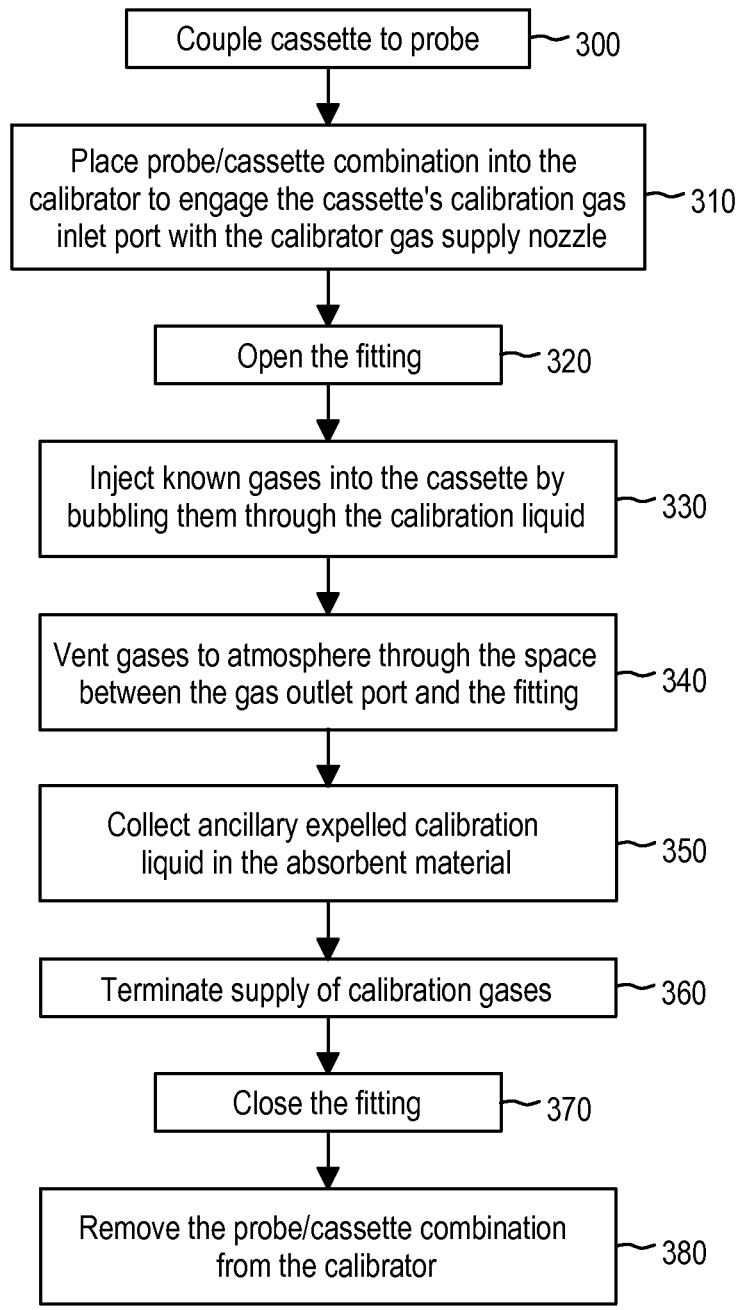
FIG. 6 is a flowchart illustrating the steps of a method of calibrating a blood parameter measurement cassette and collecting liquid discharged during venting.

FIG. 6 is a flow chart describing a method of collecting a liquid discharge generated by a venting process of a blood parameter measurement cassette during calibration. Step 300 consists of physically coupling the cassette to a blood parameter monitor probe. Next, as shown in step 310, the probe/cassette combination is placed into the calibrator device. The cassette's lower port must be positioned to engage with the calibrator's gas supply nozzle to enable calibration gas flow from the calibrator to the cassette. Then the cassette's fitting will be opened to its venting position as stated in step 320. Step 330 is the injection of calibration gas into the cassette by bubbling the calibration gas through the liquid located inside the middle chamber of the cassette. Step 340 describes the venting to atmosphere of the calibration gas as it egresses from the cassette through the space between the cassette's upper gas outlet port and the fitting. This space is also known as the egress path. As stated above, is some vestige liquid may be expelled with the venting gas, and step 350 refers to the collection of this vestige liquid by means of absorption by the absorbent material disposed at least partially in the egress path of the venting gas. Step 360 refers to the termination of the calibration gas flow after the phase of the calibration process requiring gas flow has been completed. Next, the fitting is returned to its closed position as shown in step 370. Lastly, in step 380, the probe/cassette combination is removed from the calibrator and is ready for actual use in a medical procedure with a blood parameter monitoring device.

While the invention has been described in reference to a preferred embodiment comprising a blood parameter measurement cassette, it should be understood by those skilled in the art that the essence of the invention may be applied to other fluid-handling medical devices as well. In addition, various changes may be made and equivalents may be substituted for elements thereof without departing from the essential scope of the invention. Therefore, it is intended that the invention not be limited to the particular embodiment disclosed herein, but that the invention will include all embodiments falling within the scope of the claims.

We claim:

1. A blood parameter measurement cassette having sensors which are chemically responsive to blood constituents during a medical procedure, said sensors being calibrated with a blood parameter monitoring device prior to said medical procedure, said cassette comprising:
 a main body with a longitudinal axis being oriented substantially vertically during a calibration process, wherein said main body includes a middle chamber containing a quantity of a liquid, a lower end with a first port, and an upper end with a second port, wherein during said calibration process said first port is used as a calibration gas inlet port for connection to a source of a calibration gas, wherein during said calibration process said second port is used as a gas outlet port for venting said calibration gas to atmosphere, and wherein said calibration gas being vented may induce an amount of said liquid to expel from said main body through said gas outlet port;
 a fitting coupled to said second port, said fitting including an internal luer connector along a central fluid path and adapted to receive a removable cap for selectably closing off the luer connector, said fitting being movable along the longitudinal axis between a first closed position and a second venting position, wherein while in said venting position an egress path is defined by a concentric space between an outer periphery of said main body and an inner periphery of said fitting, said egress path being used during said calibration process for venting said calibration gas to atmosphere while said luer connector is closed off; and
 an absorbent material member disposed at least partially in said egress path, wherein during said calibration process said absorbent material permits said calibration gas to vent to atmosphere while absorbing said liquid that is induced to be expelled from said main body by venting of said calibration gas;
 wherein said fitting has a lower end that is longitudinally displaced to expose said absorbent material member when in said venting position and that is longitudinally displaced to cover said concentric space and said absorbent material member when in said closed position.

2. The cassette of claim 1, wherein said absorbent material is a medical grade gauze.

3. The cassette of claim 1, wherein said absorbent material is affixed to said outer periphery of said main body by an adhesive.

4. The cassette of claim 1, wherein said absorbent material comprises a stretchable ring with an unstretched inner diameter that is smaller than an outer diameter of said main body, wherein said stretchable ring of absorbent material is secured to said outer periphery of said main body by means of a physical interference fit.

5. The cassette of claim 1, wherein said main body includes an annular flange disposed on said outer periphery, wherein said fitting includes an annular shoulder disposed on said inner periphery, and wherein said fitting while in said venting position is restrained from becoming completely detached from said main body by physical interference of said annular shoulder and said annular flange.

\* \* \* \* \*